United States Patent
Hsiao et al.

(10) Patent No.: US 10,987,398 B2
(45) Date of Patent: Apr. 27, 2021

(54) HERBAL COMPOUND EXTRACT TO MODERATE DIABETES WITH LIVER NECROSIS AND FIBROSIS AND USE THEREOF

(71) Applicant: Omics lifescience Co., Ltd., Taichung (TW)

(72) Inventors: Tzu-Chih Hsiao, Taichung (TW); Su-Cheng Lee, Taichung (TW); Chia-Fu Hsiao, Taichung (TW); Yen-Yu Hsiao, Taichung (TW)

(73) Assignee: OMICS LIFESCIENCE CO., LTD, Taichung (TW)

( * ) Notice: Subject to any disclaimer, the term of this patent is extended or adjusted under 35 U.S.C. 154(b) by 257 days.

(21) Appl. No.: 15/985,198

(22) Filed: May 21, 2018

(65) Prior Publication Data

US 2019/0351001 A1   Nov. 21, 2019

(51) Int. Cl.

| | |
|---|---|
| *A61K 36/8984* | (2006.01) |
| *A61K 36/488* | (2006.01) |
| *A61K 36/79* | (2006.01) |
| *A61K 36/484* | (2006.01) |
| *A61K 35/62* | (2006.01) |
| *A61P 3/10* | (2006.01) |
| *A61K 36/537* | (2006.01) |
| *A61P 3/06* | (2006.01) |
| *A61K 36/07* | (2006.01) |
| *A61K 36/258* | (2006.01) |
| *A61K 36/64* | (2006.01) |
| *A61P 1/16* | (2006.01) |

(52) U.S. Cl.
CPC .......... *A61K 36/8984* (2013.01); *A61K 35/62* (2013.01); *A61K 36/07* (2013.01); *A61K 36/258* (2013.01); *A61K 36/484* (2013.01); *A61K 36/488* (2013.01); *A61K 36/537* (2013.01); *A61K 36/64* (2013.01); *A61K 36/79* (2013.01); *A61P 1/16* (2018.01); *A61P 3/06* (2018.01); *A61P 3/10* (2018.01)

(58) Field of Classification Search
CPC .. A61K 2300/00; A61K 36/07; A61K 36/258; A61K 36/484; A61K 36/488; A61K 36/537; A61K 36/64; A61K 36/79; A61K 36/8984; A61K 35/62; A61P 1/16; A61P 3/06; A61P 3/10
See application file for complete search history.

(56) References Cited

U.S. PATENT DOCUMENTS

| | | | | |
|---|---|---|---|---|
| 6,964,785 | B2 * | 11/2005 | Jo | A61K 36/234 424/725 |
| 8,420,136 | B2 * | 4/2013 | Liou | A61K 36/254 424/728 |
| 9,220,738 | B1 * | 12/2015 | Lee | A61K 36/533 |
| 9,301,987 | B2 * | 4/2016 | Gokaraju | A61K 36/328 |
| 9,345,732 | B2 * | 5/2016 | Gokaraju | A23L 33/105 |
| 10,561,699 | B2 * | 2/2020 | Liou | A61K 36/481 |
| 2019/0336884 | A1 * | 11/2019 | Makerri | B01D 11/00 |

FOREIGN PATENT DOCUMENTS

| | | | | |
|---|---|---|---|---|
| AU | 2009298177 A1 * | 4/2010 | | A61K 2300/00 |
| WO | WO-2010040058 A1 * | 4/2010 | | A61K 2300/00 |

* cited by examiner

*Primary Examiner* — Aaron J Kosar
(74) *Attorney, Agent, or Firm* — Muncy, Geissier, Olds & Lowe, P.C.

(57) ABSTRACT

The present disclosure relates to a herbal compound extract to moderate diabetes with liver necrosis and fibrosis and applications thereof wherein a herbal compound consists of 10 to 20 units rhizome of *Dendrobium nobile* Lindl, 6 to 12 units fruiting body of *Antrodia camphorata*, 12 to 20 units root of *Panax ginseng* C. A. Mey, 10 to 30 units root of *Rehmannia glutinosa* Libosch, 15 to 30 units rhizome of *Salvia miltiorrhiza* Bge., 6 to 12 units all of *Pheretima asperfillm* (E. Perrier), 10 to 30 units root of *Pueraria mirifica*, 8 to 15 units fruit of *Schisandra chinensis* (Turcz.) Baill and 6 to 8 units rhizome of *Glycyrrhiza uralensis* Fisch and the herbal compound extract is able to moderate symptoms comprising hyperglycemia, hyperlipidemia, abnormal liver function about liver necrosis and fibrosis due to the diabetes.

21 Claims, 4 Drawing Sheets

200X

200X

HERBAL COMPOUND EXTRACT TO MODERATE DIABETES WITH LIVER NECROSIS AND FIBROSIS AND USE THEREOF

FIELD OF THE INVENTION

The invention relates to a herbal compound extract, particularly to a medicinal and edible formula or a food formula to moderate hyperglycemia, hyperlipidemia, abnormal liver function on diabetes with liver necrosis and fibrosis effectively.

BACKGROUND OF THE INVENTION

Statistically, 60%~80% and 22%~34% patients with Type 2 diabetes mellitus (T2DM) also suffer from the non-alcoholic fatty liver disease (NAFLD) and progressive liver fibrosis, respectively. In 2005, Scott L. Friedman, the leading expert on liver fibrosis in the United States, argued a viewpoint of "liver fibrosis and even liver cirrhosis being reversible".

NAFLD, which is a metabolic stress-induced liver disease, which is closely relates to insulin resistance and genetics, is attributed to some risk hazards, for example, high fat and high sucrose diet (HFSD), insulin resistance, metabolic syndrome and others including obesity, hypertension, dyslipidemia and T2DM.

For a patient who has fallen chronic liver disease about necrosis or liver fibrosis is invasible but reversible and draws more attentions, in contrast to liver cirrhosis that is irreversible. In the progress of liver fibrosis, extracellular matrix, which consist of collagenous fibers, dominantly are synthesized, but are increasingly and modestly degraded and deposited in the liver excessively from which dynamic disequilibrium between syntheses and degradations of extracellular matrix is observed.

The biochemical abnormality during liver fibrosis has much to do with impaired metabolism of hepatic cells. In a patient with poor liver function, some index are high: AST; ALT; GGT; Alb; reactive oxygen species (ROS; tumor necrosis factor-α (TNF-α) and interferon-6 (IL-6) (inflammatory factor index); transforming growth factor-β1 (TGF-β1); fibrinogen (Fbg); IV-Collagen and fibronectin (FN); Smad2, Smad3, pSmad2, pSmad3 and alpha smooth muscle actin (α-SMA). On the other hand, some index are low: MMP1, MMP2 and MMP9.

When excessive free radicals of liver tissues are produced by HFSD, hepatic stellate cells activated by a great number of ROS cause hepatocellular injuries and triggering liver fibrosis. For an injured liver, inflammatory factors including TNF-α and IL-6 that are released by activated Kupffer cells, resulting in inflammatory cell infiltration and cytotoxicity.

Activating hepatic stellate cells directly or indirectly, TGF-β1, as the strongest pro-fibrogenic, factor prompts hepatic cells to synthesize extracellular matrix but inhibits decompositions of extracellular matrix. TGF-β1 activated extracellularly and binding TβRII is able to activate serine or serine-threonine kinase in a receptor's intracellular domain. TβRI and TβRII, both of which constitute the heteropolymers inside the receptor, further activate intracellular kinase of TβRI, phosphorylating Smad2 as well as Smad3, and binding Smad4. While shifted to a nucleus, Smad2, Smad3 and Smad4 proteins can complete transmembrane signal transduction, affect relative genetic transcription and cause syntheses of extracellular matrix by hepatic cells.

The hepatic stellate cells activated in an injured liver induces protein expressions and phosphorylation of Smad2 and Smad3, both of which are further transferred to a nucleus for completion of transmembrane signal transduction and aggravation of α-SMA that exacerbates accumulated fibrinogen, IV-Collagen and fibronectin.

For syntheses of extracellular matrix in the pathological process of liver fibrosis, hepatic stellate cells as target cells of various cell factors display changes in cell proliferations/activations and take part in syntheses and depositions of extracellular matrix under regulations of complex cellular signal transductions. Hepatic stellate cells, which play a dominant role in the progress of liver fibrosis, are the main sources of matrix metalloproteinases (MMPs) that exert co-regulated actions to prompt protein expressions of MMP1, MMP2 and MMP9, but inhibit productions of Type-I, III and IV collagens.

In order to evaluate liver fibrosis, the pathologic changes are displayed on the collagenous fiber structures with hyaline degenerations that are deposited around the interlobular artery/vein and the bile duct and exacerbate hepatocyte swelling, ballooning degenerations, spotty necrosis, unclear boundaries among hepatic cells, narrower hepatic sinusoid, microangiopathy particularly around the central vein, accumulations of collagenous fibers in connective tissues and diabetes with liver fibrosis.

Diabetes with liver necrosis and fibrosis has been drawing more attentions. In this regard, the issues relating to the hepatic stellate cells which play a key role in the progress of diabetes with liver necrosis and fibrosis still deserve to be studied because therapies, medications and/or food formulas with fewer side effects are needed. Accordingly, providing a nontoxic herbal compound extract with fewer side effects for moderating diabetes with liver necrosis and fibrosis is the subject for research by persons skilled in the art.

SUMMARY OF THE INVENTION

The present disclosure is directed to a herbal compound extract for moderate diabetes with liver necrosis and fibrosis wherein raw materials of a herbal compound comprise rhizome of *Dendrobium nobile* Lindl, fruiting body of *Antrodia camphorata*, root of *Panax ginseng* C. A. Mey, root of *Rehmannia glutinosa* Libosch, rhizome of *Salvia miltiorrhiza* Bge., all of *Pheretima asperfillm* (E. Perrier), root of *Pueraria mirifica*, fruit of *Schisandra chinensis* (Turcz.) Baill. and rhizome of *Glycyrrhiza uralensis* Fisch.

Further, the raw materials for the effective components for preparation of the herbal compound according the present disclosure by weight (i.e., relative unit numbers of a unit weight) comprise 10 to 20 units rhizome of *Dendrobium nobile* Lindl, 6 to 12 units fruiting body of *Antrodia camphorata*, 12 to 20 units root of *Panax ginseng* C. A. Mey, 10 to 30 units root of *Rehmannia glutinosa* Libosch, 15 to 30 units fruit of *Salvia miltiorrhiza* Bge., 6 to 12 units all of *Pheretima asperfillm* (E. Perrier), 10 to 30 units root of *Pueraria mirifica*, 8 to 15 units fruit of *Schisandra chinensis* (Turcz.) Baill. and 6 to 8 units rhizome of *Glycyrrhiza uralensis* Fisch.

The raw materials for the effective composition for preparation of the herbal compound by weight comprise 20 units rhizome of *Dendrobium nobile* Lindl, 6 units fruiting body of *Antrodia camphorata*, 20 units root of *Panax ginseng* C. A. Mey, 15 units root of *Rehmannia glutinosa* Libosch, 15 units fruit of *Salvia miltiorrhiza* Bge., 9 units all of *Pheretima asperfillm* (E. Perrier), 15 units root of *Pueraria*

*mirifica*, 8 units fruit of *Schisandra chinensis* (Turcz.) Baill. and 8 units rhizome of *Glycyrrhiza uralensis* Fisch.

The raw materials for the effective composition for preparation of the herbal compound by weight comprise 10 units rhizome of *Dendrobium nobile* Lindl, 12 units fruiting body of *Antrodia camphorata*, 20 units root of *Panax ginseng* C. A. Mey, 30 units root of *Rehmannia glutinosa* Libosch, 30 units fruit of *Salvia miltiorrhiza* Bge., 12 units all of *Pheretima asperfillm* (E. Perrier), 10 units root of *Pueraria mirifica*, 10 units fruit of *Schisandra chinensis* (Turcz.) Baill. and 8 units rhizome of *Glycyrrhiza uralensis* Fisch.

The raw materials for the effective composition for preparation of the herbal compound by weight comprise 15 units rhizome of *Dendrobium nobile* Lindl, 9 units fruiting body of *Antrodia camphorata*, 12 units root of *Panax ginseng* C. A. Mey, 10 units root of *Rehmannia glutinosa* Libosch, 15 units of fruit *Salvia miltiorrhiza* Bge., 12 units all of *Pheretima asperfillm* (E. Perrier), 15 units root of *Pueraria mirifica*, 15 units fruit of *Schisandra chinensis* (Turcz.) Baill. and 6 units rhizome of *Glycyrrhiza uralensis* Fisch.

The raw materials for the effective composition for preparation of the herbal compound by weight comprise 15 units rhizome of *Dendrobium nobile* Lindl, 9 units fruiting body of *Antrodia camphorata*, 12 units root of *Panax ginseng* C. A. Mey, 18 units root of *Rehmannia glutinosa* Libosch, 15 units fruit of *Salvia miltiorrhiza* Bge., 6 units all of *Pheretima asperfillm* (E. Perrier), 15 units root of *Pueraria mirifica*, 15 units fruit of *Schisandra chinensis* (Turcz.) Baill. and 6 units rhizome of *Glycyrrhiza uralensis* Fisch.

The herbal compound extract is a powder agent to concoct each of a solution, a suspending liquid, an emulsion, a syrups, a pill, a buccal tablet, a tablet, a capsule and a pastille.

The herbal compound extract is a medicinal and edible formula or a food formula.

The herbal compound extract is able to moderate body weight, weight of liver tissues, weight of abdominal adipose, hyperglycemia, hyperlipidemia, liver necrosis or fibrosis.

A use of the herbal compound extract to moderate diabetes with liver necrosis and fibrosis based on a medicinal and edible formula or a food formula are provided in the present disclosure wherein raw materials of a herbal compound comprise rhizome of *Dendrobium nobile* Lindl, fruiting body of *Antrodia camphorata*, root of *Panax ginseng* C. A. Mey, root of *Rehmannia glutinosa* Libosch, fruit of *Salvia miltiorrhiza* Bge., all of *Pheretima asperfillm* (E. Perrier), root of *Pueraria mirifica*, fruit of *Schisandra chinensis* (Turcz.) Baill. and rhizome of *Glycyrrhiza uralensis* Fisch.

The raw materials for the effective composition for preparation of the herbal compound by weight comprise 10 to 20 units rhizome of *Dendrobium nobile* Lindl, 6 to 12 units fruiting body of *Antrodia camphorata*, 12 to 20 units root of *Panax ginseng* C. A. Mey, 10 to 30 units root of *Rehmannia glutinosa* Libosch, 15 to 30 units fruit of *Salvia miltiorrhiza* Bge., 6 to 12 units of all of *Pheretima asperfillm* (E. Perrier), 10 to 30 units root of *Pueraria mirifica*, 8 to 15 units fruit of *Schisandra chinensis* (Turcz.) Baill. and 6 to 8 units rhizome of *Glycyrrhiza uralensis* Fisch.

The raw materials for the effective composition for preparation of the herbal compound by weight comprise 20 units rhizome of *Dendrobium nobile* Lindl, 6 units fruiting body of *Antrodia camphorata*, 20 units of root of *Panax ginseng* C. A. Mey, 15 units of root of *Rehmannia glutinosa* Libosch, 15 units fruit of *Salvia miltiorrhiza* Bge., 9 units all of *Pheretima asperfillm* (E. Perrier), 15 units root of *Pueraria mirifica*, 8 units fruit of *Schisandra chinensis* (Turcz.) Baill. and 8 units rhizome of *Glycyrrhiza uralensis* Fisch.

The raw materials for the effective composition for preparation of the herbal compound by weight comprise 10 units rhizome of *Dendrobium nobile* Lindl, 12 units fruiting body of *Antrodia camphorata*, 20 units root of *Panax ginseng* C. A. Mey, 30 units of root of *Rehmannia glutinosa* Libosch, 30 units fruit of *Salvia miltiorrhiza* Bge., 12 units all of *Pheretima asperfillm* (E. Perrier), 10 units root of *Pueraria mirifica*, 10 units fruit of *Schisandra chinensis* (Turcz.) Baill. and 8 units rhizome of *Glycyrrhiza uralensis* Fisch.

The raw materials for the effective composition for preparation of the herbal compound by weight comprise 15 units rhizome of *Dendrobium nobile* Lindl, 9 units fruiting body of *Antrodia camphorata*, 12 units root of *Panax ginseng* C. A. Mey, 10 units of root of *Rehmannia glutinosa* Libosch, 15 units fruit of *Salvia miltiorrhiza* Bge., 12 units all of *Pheretima asperfillm* (E. Perrier), 15 units root of *Pueraria mirifica*, 15 units fruit of *Schisandra chinensis* (Turcz.) Baill. and 6 units rhizome of *Glycyrrhiza uralensis* Fisch.

The raw materials for the effective composition for preparation of the herbal compound by weight comprise 15 units rhizome of *Dendrobium nobile* Lindl, 9 units fruiting body of *Antrodia camphorata*, 12 units root of *Panax ginseng* C. A. Mey, 18 units of root of *Rehmannia glutinosa* Libosch, 15 units fruit of *Salvia miltiorrhiza* Bge., 6 units all of *Pheretima asperfillm* (E. Perrier), 15 units root of *Pueraria mirifica*, 15 units fruit of *Schisandra chinensis* (Turcz.) Baill. and 6 units rhizome of *Glycyrrhiza uralensis* Fisch.

The herbal compound extract is able to moderate body weight, weight of liver tissues, weight of abdominal adipose, fasting blood glucose (FBG), total cholesterol (TC), triglyceride (TG), aspartate aminotransferase (AST) and alanine aminotransferase (ALT) of a patient suffering from diabetes with liver necrosis and fibrosis.

The herbal compound extract is able to moderate foamy degeneration, hepatocyte swelling, unclear boundaries among hepatic cells, narrower hepatic sinusoid, slight lymphocytes infiltration around the central vein and portal areas, and accumulated collagenous fibers of connective tissues in liver tissues of a patient suffering from diabetes with necrosis and fibrosis.

The herbal compound extract is able to moderate accumulations of collagenous fibers including α-SMA, fibrinogen, IV-Collagen and fibronectin of a patient suffering from diabetes with liver necrosis and fibrosis.

The herbal compound extract is able to moderate diabetes with liver necrosis and fibrosis by inhibiting ROS, inflammation of TNF-α/IL-6 and the signaling pathways of liver fibrosis from TGFβ1 to Smads/α-SMA.

The herbal compound extract is able to promote protein expressions of MMP1, MMP2 and MMP9, decompose more collagenous fibers and moderate diabetes with liver necrosis and fibrosis by inhibiting Smad2, Smad3 and α-SMA.

The herbal compound extract as a medicinal and edible formula or a food formula is characteristic of the oral dosage of 20-40 g per day.

DETAILED DESCRIPTION OF THE PREFERRED EMBODIMENTS

Figure 1:
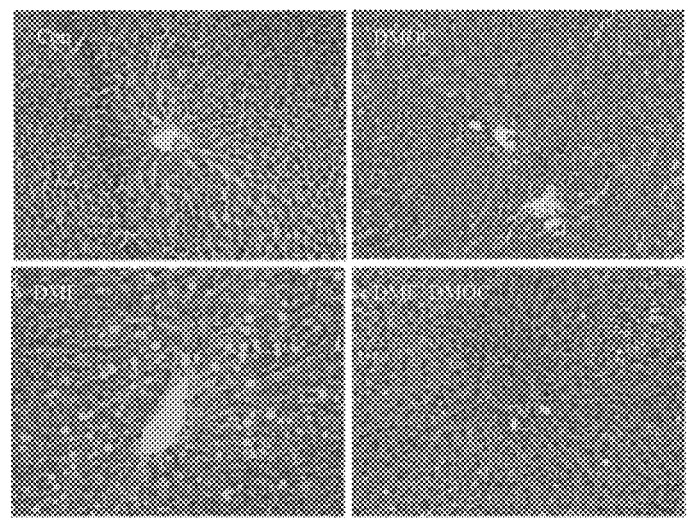
FIG. 1 Illustrates changes in rats' liver injuries checked with the HE stain assay.

The technical and scientific terminology in the present application is comprehensible to the persons skilled in the art, unless otherwise defined herein.

In the present disclosure, a herbal compound extract is prepared on the basis of weight for treatments of hyperglycemia, hyperlipidemia, abnormal liver function and liver fibrosis and has been tested repeatedly by the applicant for development of the dendrobium mixture in order cycle (DMOC) method. The recommended dosages by weight (i.e., relative unit numbers of a unit weight) of the DMOC-based herbal compound extract comprising 10 to 20 units rhizome of *Dendrobium nobile* Lindl, 6 to 12 units fruiting body of *Antrodia camphorata*, 12 to 20 units root of *Panax ginseng* C. A. Mey, 10 to 30 units of root of *Rehmannia glutinosa* Libosch, 15 to 30 units fruit of *Salvia miltiorrhiza* Bge., 6 to 12 units all of *Pheretima asperfillm* (E. Perrier), 10 to 30 units root of *Pueraria mirifica*, 8 to 15 units fruit of *Schisandra chinensis* (Turcz.) Baill. and 6 to 8 units rhizome of *Glycyrrhiza uralensis* Fisch for a human being and a rat are 20-40 g per day, which refers to "the maximum safe starting dose in initial clinical trials for therapeutics in adult healthy volunteers" published by USFDA in 2005, and an optimal dose based on the conversion factor of 6 to convert weight between a human being and a mouse, respectively.

The herbal compound extract in the present disclosure may be taken as one application amid foods, drinks, healthy foods, additives in potable water for animals, additives in animal feeds, veterinary drugs, medicinal products of human beings, food additives and beverage additives.

Embodiment 1: Preparation and Administration of the DMOC-Based Herbal Compound Extract The 130 g dried and pulverized DMOC-based herbal compound comprising 10 to 20 units rhizome of *Dendrobium nobile* Lindl, 6 to 12 units fruiting body of *Antrodia camphorata*, 12 to 20 units root of *Panax ginseng* C. A. Mey, 10 to 30 units of root of *Rehmannia glutinosa* Libosch, 15 to 30 units fruit of *Salvia miltiorrhiza* Bge., 6 to 12 units all of *Pheretima asperfillm* (E. Perrier), 10 to 30 units root of *Pueraria mirifica*, 8 to 15 units fruit of *Schisandra chinensis* (Turcz.) Baill. and 6 to 8 units rhizome of *Glycyrrhiza uralensis* Fisch as well as 80% ethyl alcohol by weight (i.e., relative unit numbers of a unit weight) were mixed with each other uniformly based on the ratio of 1:15 for extraction by ultrasonic oscillation at 65° C. in the next two hours; the liquid therefrom was filtered out and placed in a rotary heater for volatilization of ethyl alcohol and concentration of alcoholic solutions, and then processed for two alcoholic extractions and one water extraction. Finally, the 100 ml alcoholic solutions concentrated from ethyl alcohol and 50 ml aqueous solutions derived from water extraction were mixed and concentrated as 50 ml solutions; then, the 50 ml concentrated solutions in which maltodextrin was added were processed for spray-drying and development of 20-40 g powders.

The specific formulas for preparation of the herbal compound according to the present application are shown as follows.

Formula 1: 20 units rhizome of *Dendrobium nobile* Lindl, 6 units fruiting body of *Antrodia camphorata*, 20 units root of *Panax ginseng* C. A. Mey, 15 units of root of *Rehmannia glutinosa* Libosch, 15 units fruit of *Salvia miltiorrhiza* Bge., 9 units all of *Pheretima asperfillm* (E. Perrier), 15 units root of *Pueraria mirifica*, 8 units fruit of *Schisandra chinensis* (Turcz.) Baill. and 8 units rhizome of *Glycyrrhiza uralensis* Fisch;

Formula 2: 10 units rhizome of *Dendrobium nobile* Lindl, 12 units fruiting body of *Antrodia camphorata*, 20 units root of *Panax ginseng* C. A. Mey, 30 units root of *Rehmannia glutinosa* Libosch, 30 units fruit of *Salvia miltiorrhiza* Bge., 12 units all of *Pheretima asperfillm* (E. Perrier), 10 units root of *Pueraria mirifica*, 10 units fruit of *Schisandra chinensis* (Turcz.) Baill. and 8 units rhizome of *Glycyrrhiza uralensis* Fisch;

Formula 3: 15 units rhizome of *Dendrobium nobile* Lindl, 9 units fruiting body of *Antrodia camphorata*, 12 units root of *Panax ginseng* C. A. Mey, 10 units of root of *Rehmannia glutinosa* Libosch, 15 units fruit of *Salvia miltiorrhiza* Bge., 12 units all of *Pheretima asperfillm* (E. Perrier), 15 units root of *Pueraria mirifica*, 15 units fruit of *Schisandra chinensis* (Turcz.) Baill. and 6 units rhizome of *Glycyrrhiza uralensis* Fisch; and Formula 4: 15 units rhizome of *Dendrobium nobile* Lindl, 9 units fruiting body of *Antrodia camphorata*, 12 units root of *Panax ginseng* C. A. Mey, 18 units of root of *Rehmannia glutinosa* Libosch, 15 units fruit of *Salvia miltiorrhiza* Bge., 6 units all of *Pheretima asperfillm* (E. Perrier), 15 units root of *Pueraria mirifica*, 15 units fruit of *Schisandra chinensis* (Turcz.) Baill. and 6 units rhizome of *Glycyrrhiza uralensis* Fisch;

In the present disclosure, the herbal compound is a powder-based potable beverage. According to the Embodiment 1, the 130 g dried and pulverized herbal compound and 80% ethyl alcohol were mixed with each other uniformly based on the ratio of 1:15 for extraction by ultrasonic oscillation at 65° C. in the next two hours; the liquid therefrom was filtered out and placed in a rotary heater for volatilization of ethyl alcohol and concentration of alcoholic solutions, and then processed for two alcoholic extractions and one water extraction. Finally, the 100 ml alcoholic solutions concentrated from ethyl alcohol and 50 ml aqueous solutions derived from water extraction, each of which was mixed with maltodextrin, were processed for spray-drying after which 30 g powders as an ingredient of a potable beverage were produced.

The specific effects of the herbal compound extract are further demonstrated in data of clinic trails.

Material and Method:

40 male SD rats at 5 weeks of age (weight: 180±10 g) fed adaptively for one week were assigned to the following four groups randomly (based on the Random Number Table).

Group① "Con" group: 10 rats were fed with normal diets;

Group② "DMOC" group: 10 rats were fed with normal diets and the dendrobium mixtures;

Group③ "Diabetes mellutus fibrosis, DMF" group: 10 rats suffering from diabetes mellitus with liver necrosis and fibrosis were fed with high fat-high sucrose diets (HFSD) and treated with Streptozotocin (STZ) twice;

Group④ "DMF+DMOC" group: 10 rats suffering from diabetes with liver necrosis and fibrosis were fed with high fat-high sucrose diets (HFSD) and treated with STZ twice in the beginning and fed with the dendrobium mixtures later.

Groups ① & ② were normal control groups; groups ③ & ④ were model groups.; groups ② & ④ were induced groups. The rats in all groups were fed with appropriate diets as shown in Table 1 and RO water in the first four weeks and fasted but fed with water in the next 12 hours. The rats in Groups ③ & ④ were given Streptozotocin (STZ) twice at intraperitoneal injections (25 mg/kg+m² & 72 hours apart). Then, the levels of fasting blood glucose of rats given STZ were measured by the oxidase assay at the fourth day after injections for development of the animal model of diabetic rats with fasting blood glucose levels higher than 11.1 mmol/L. As shown in the model of Groups ③ & ④, the symptoms including hyperglycemia, hyperlipidemia and abnormal liver function were observed in rats fed with HFSD on liver necrosis and fibrosis was found in rats of Groups ③ & ④ at Week 36 obviously in the designed experiment. The rats in Groups ② and ④ were interfered by DMOC and weighed up once every week for adjusted intragastric feeding from Week 36 to Week 44 and checks after 44 weeks.

TABLE 1

Ingredients and calories in diets

| Ingredient (g/kg) | Diet for normal control groups | HFSD for induced groups |
| --- | --- | --- |
| Corn starch | 9.75 | 5.00 |
| Casein | 20.00 | 20.00 |
| Maltodextrin | 13.20 | — |
| Sucrose | 10.00 | 34.80 |
| Soybean oil | 7.00 | 5.00 |
| Lard | — | 15.50 |
| Cellulose | 5.00 | 5.00 |
| AIN 93G Mineral Mix | 3.50 | 3.50 |
| AIN 93 Vitamin Mix | 1.00 | 1.00 |
| L-Cystine | 0.30 | 0.30 |
| Choline Bitartrate | 0.25 | 0.25 |
| t-bytylhydroquinone | 0.0014 | 0.01 |
| Calories (kcal/g) | 3.96 | 4.65 |
| Carbohydrate | 63.6% | 42.8% |
| Protein | 20.5% | 17.5% |
| Fat | 15.9% | 39.7% |

The dosage of Sreptozosin (STZ), an experimental drug, prepared for tests was 25 mg/kg+m² for rats with the weight lower than 200 g or calculated by the body surface area of a rat with the weight greater than 200 g. STZ was dissolved in 0.1 mol/L sodium citrate buffers (pH=4.2) in dark and ice-bath conditions for preparation of 1% solutions; then, the 1% solutions in which PBS and dry paraformaldehyde powders were added were kept in a thermostatic chamber at 37° C.

The health status of rats in each group such as body weight, organ weight and various indices including BG, TC, TG, AST, ALT, ROS, TNF-α, IL-6 and TGF-β1 conducted in serological tests were checked; the changes in liver fibrosis were checked with the hematoxylin eosin stain (HE stain) and the Masson's trichrome stain; the changes of α-SMA, fibrinogen, IV-Collagen, fibronectin levels in liver tissues were checked by the immunohistochemistry (IHC) assay; the changes in protein expressions of Smad2, Smad3, pSmad2, pSmad3, α-SMA, MMP1, MMP2 and MMP9 were checked by the Western blot (WB) assay.

Embodiment 2: Diabetes with Liver Necrosis and Fibrosis Moderated by DMOC

Changes in Rats' Appearances

The success rates of modeling for Groups ① & ② (normal control groups) and Groups ③ & ④ (induced groups), in which no rat died, were 100% during the tests. The rats in normal control groups displayed good conditions as follows: good appetite and water intake, moderate urine output, body weight increasing steadily, agility, lustrous fur and granular feces. In contrast, the rats in the induced groups fed with calorie-rich HFSD which made a difference to the total food intake displayed as follows: poor appetite, moderate water intake, more urine output, stable body weight (in first two months), soaring body weight (from Month 3), dispirited status, drowsiness, lackluster hair and loose stool.

Changes of Body Weight in Rats

The changes of body weight in rats interfered by DMOC are shown in Table 2. There was no significant difference in body weight of rats between "Con" and "DMOC" (P>0.05). Before interference of DMOC, the body weight of rats fed with HFSD and treated with STZ intraperitoneal injections were significantly higher than those of rats in "Con" and the differences have statistical significance (P<0.01). After interference of DMOC, the body weight of rats in "DMF+DMOC" were significantly lower than those of rats in "DMF" and the differences have statistical significance (P<0.01). As shown in the test results, diabetes can cause the body weight gain and DMOC can improve the changes in body weight gains.

Changes of Liver Tissue Weight in Rats

The changes of liver tissue weight in rats interfered by DMOC are shown in Table 2. There was no significant difference in liver tissue weight of rats between "Con" and "DMOC" (P>0.05). Before interference of DMOC, the liver tissue weight of rats fed with HFSD and treated with STZ intraperitoneal injections were significantly higher than those of rats in "Con" and the differences have statistical significance (P<0.05). After interference of DMOC, the liver tissue weight of rats in "DMF+DMOC" were significantly lower than those of rats in "DMF" and the differences have statistical significance (P<0.05). As shown in test results, diabetes can make liver tissues swollen and DMOC can improve the changes in liver tissues weight.

Changes of Abdominal Adipose Weight in Rats

The changes of abdominal adipose weight in rats interfered by DMOC are shown in Table 2. There was no significant difference in abdominal adipose weight of rats between "Con" and "DMOC" (P>0.05). Before interference of DMOC, the abdominal adipose weight of rats fed with HFSD and treated with STZ intraperitoneal injections were significantly higher than those of rats in "Con" and the differences have statistical significance (P<0.01). After interference of DMOC, the abdominal adipose weight of rats in "DMF+DMOC" were significantly lower than those of rats in "DMF" and the differences have statistical significance (P<0.05). As shown in the test results, the accumulated abdominal adipose weight of rats attributed to diabetes was moderated by DMOC.

TABLE 2

Changes of body weight, liver tissue weight and abdominal adipose weight in rats ($\bar{x} \pm s$)

| Group | N | Body weight (g) | Liver tissue weight (g) | Abdominal adipose weight (g) |
|---|---|---|---|---|
| Con | 10 | 626.00 ± 50.10 | 16.11 ± 2.00 | 36.99 ± 4.80 |
| DMOC | 10 | 586.70 ± 31.50 | 16.24 ± 2.90 | 28.17 ± 2.80 |
| DMF | 10 | 781.70 ± 114.90## | 19.08 ± 2.40# | 93.90 ± 21.40## |
| DMF + DMOC | 10 | 654.80 ± 51.30** | 16.05 ± 1.30* | 73.30 ± 16.00* |

Note 1:
compared with "Con" (P < 0.05), and
compared with "Con" (P < 0.01);
Note 2:
*compared with "DMF" (P < 0.05), and
**compared with "DMF" (P < 0.01)

Changes in Rats' FBG (Fasting Blood Glucose) Level

The measurement of the FBG level in the serum is based on the oxidase assay. 10 μL serums and 1 mL test solutions from the Glucose Enzymatic Kit (Audit Diagnostics, Cork, Ireland), both of which were mixed together, acted with each other at 37° C. for five minutes and were tested by the oxidase assay that relies on a spectrophotometer to measure absorbance at the wavelength of 500 nm as the basis of comparison with the standard sample for estimation of the glucose level in the serum according to the formula as follows:

$$\text{Glucose (mg/dL)} = (\text{Sample} - \text{Blank}) / (\text{Calibrator} - \text{Blank}) \times 100$$

The changes in rats' FBG levels interfered by DMOC are shown in Table 3. There was no significant difference in FBG levels of rats between "Con" and "DMOC" (P>0.05). Before interference of DMOC, the FBG level of rats fed with HFSD and treated with STZ intraperitoneal injections was significantly higher than that of rats in "Con" and the difference has statistical significance (P<0.01). After interference of DMOC, the FBG level of rats in "DMF+DMOC" was significantly lower than that of rats in "DMF" and the difference has statistical significance (P<0.01). As shown in test results, the FBG level of rats after induction increased significantly and was greater than 11.1 mmol/L, which means rats suffering from diabetes, and the FBG level of diabetic rats was moderated by DMOC effectively.

Changes in Rats' Serum Lipid Level

The total cholesterol (TC) level in the serum was measured in an automatic biochemical analyzer. 10 μL serums and 1 mL test solutions from the Cholesterol Enzymatic Kit (Audit Diagnostics), both of which were mixed together, acted with each other at 37° C. for five minutes and were tested by an automatic biochemical analyzer that relies on a spectrophotometer to measure absorbance at 500 nm as the basis of comparison with the standard sample for estimation of the serum cholesterol level according to the formula as follows:

$$\text{Total Cholesterol (mg/dL)} = (\text{Sample} - \text{Blank}) / (\text{Calibrator} - \text{Blank}) \times 200$$

The triglyceride (TG) level in the serum was measured in an automatic biochemical analyzer. 10 μL serums and 1 mL test solutions from the Triglyceride Enzymatic Kit (Audit Diagnostics), both of which were mixed together, acted with each other at 37° C. for five minutes and were tested by an automatic biochemical analyzer that relies on a spectrophotometer to measure absorbance at the wavelength of 510 nm as the basis of comparison with the standard sample for estimation of the serum TG level according to the formula as follows: Triglyceride (mg/dL)=(Sample−Blank)/(Calibrator−Blank)×200

The changes in rats' serum lipid levels interfered by DMOC are shown in Table 3. There was no significant difference in TC and TG levels of the rats between "Con" and "DMOC" (P>0.05). Before interference of DMOC, the TC and TG levels of rats fed with HFSD and treated with STZ intraperitoneal injections were significantly higher than those of rats in "Con" and the differences have statistical significance (P<0.01). After interference of DMOC, the TC and TG levels of rats in "DMF+DMOC" were significantly lower than those of rats in "DMF" (P<0.05), particularly the TG level which was close to a normal value, and the differences have statistical significance (P<0.01). As shown in test results, the serum lipid levels of rats suffering from chronic diabetes increased gradually and the TC and TG levels of diabetic rats were moderated by DMOC effectively.

Changes in Rats' Liver Functions

AST (aspartate amino transferase) and ALT (alanine aminotransferase) levels in serums were measured in an automatic biochemical analyzer. The blood samples having rested at room temperature for one hour were placed inside a centrifugal machine with which serums were centrifuged at 3500 rpm and 4° C. after 20 minutes. The AST and ALT levels in serums were measured with an automatic biochemical analyzer and test specimens. With the specific test specimens for each analysis in experimental steps placed in a blood analyzer, 10 μL serums were instilled for collections of test data and statistic analysis.

As indicators to display severity of any liver injury, both AST and ALT released to blood from liver tissues obviously can be tested in serums. The changes in rats' liver functions interfered by DMOC are shown in Table 3. There was no significant difference in rats' liver functions between "Con" (Group 1) and "DMOC" (Group 2) (P>0.05). Before interference of DMOC, the AST and ALT levels of rats fed with HFSD and treated with STZ intraperitoneal injections were significantly higher than those of rats in "Con" and the differences have statistical significance (P<0.01). After interference of DMOC, the AST level of rats in "DMF+DMOC" was significantly lower than that of rats in "DMF" and the difference has statistical significance (P<0.05). Furthermore, there was no significant difference in the ALT level of rats between "DMF+DMOC" and "DMF" but the ALT level of rats in "DMF+DMOC" was 20 percent less than that of rats in "DMF". As shown in test results, the rats' hepatic cells were not injured by toxicity from drugs themselves or drug metabolites but the liver injury was attributed to diabetes. When hepatic cells injured seriously and hepatonecrosis are detected, the ratio of AST to ALT will be greater than 1. With the function to inhibit more AST than ALT, DMOC is favorable to moderating the injury of hepatocellular mitochondria attributed to diabetes.

TABLE 3

Changes of FBG, TC, TG, AST and ALT levels in rats($\bar{x} \pm s$)

| Group | N | FBG (mmol/L) | TC (mmol/L) | TG (mmol/L) | AST (U/L) | ALT (U/L) |
|---|---|---|---|---|---|---|
| Con | 10 | 5.25 ± 0.12 | 1.83 ± 0.35 | 1.06 ± 0.21 | 83.67 ± 5.20 | 35.50 ± 10.33 |
| DMOC | 10 | 4.63 ± 1.91 | 2.06 ± 0.41 | 1.03 ± 0.23 | 83.13 ± 19.80 | 37.63 ± 14.04 |
| DMF | 10 | 14.99 ± 3.95## | 2.82 ± 0.55## | 1.83 ± 0.53## | 145.00 ± 34.66## | 113.33 ± 37.45## |
| DMF + DMOC | 10 | 9.57 ± 2.87** | 2.26 ± 0.23* | 1.18 ± 0.23** | 103.00 ± 22.41* | 91.29 ± 13.88 |

Note 1:
compared with "Con" ($P < 0.01$);
Note 2:
*compared with "DMF" ($P < 0.05$), and
**compared with "DMF" ($P < 0.01$)

ROS (Reactive Oxygen Species) Level in Serums Measured with the DCF (Dichlorofluorescein) Assay With non-fluoresced DCFH-DA oxidized by ROS in cells for development of fluoresced 2',7'-dichlorofluorescein (DCF), the change in fluorescence of DCF is an indicator to evaluate the ROS level of cells. 100 μl tissue homogenates diluted with PBS and 100 μl DCFH-DA dissolved with DMSO (20 μM), both of which were mixed with each other uniformly, were added into a microdial for five-minute dark incubation and measurement of fluorescence by a fluorescence spectrometer based on the excitation wavelength of 485 nm and the emission wavelength of 520 nm.

Excessive or attenuate ROS activated by HFSD-induced oxidative stress can stimulate activation and proliferation of hepatic stellate cells directly which set off injuries and imbalance of tissues and further hepatic fibrosis. The changes in rats' ROS level interfered by DMOC are shown in Table 4. There was no significant difference in the ROS levels of rats between "Con" and "DMOC" ($P>0.05$). Before interference of DMOC, the ROS level of rats fed with HFSD and treated with STZ intraperitoneal injections was significantly higher than that of rats in "Con" and the difference has statistical significance ($P<0.01$). After interference of DMOC, the ROS level of rats in "DMF+DMOC" was significantly lower than that of rats in "DMF" and the difference has statistical significance ($P<0.01$). As shown in test results, the change in the ROS level induced by liver inflammation of diabetic rats can be moderated by interference of DMOC.

TNF-α, IL-6 and TGF-β1 Levels in Serums Measured with ELISA (Enzyme-Linked Immuno-Sorbent Assay)

In this research, 3-4 mL fasting venous blood collected in the early morning was centrifuged in a centrifugal machine at 3,000 rpm and 4° C. for 15 minutes; then, 0.5-1.0 mL supernatant was fetched with a micropipettor and kept at −80° C. for following tests without a freeze-thaw cycle. All test steps were strictly compliant with instructions of the ELISA kit manufactured by Genzyme, U.S.A. A 96-well microplate in which 100 μL Capture antibodies were added was sealed and frozen in a refrigerator at 4° C. for overnight incubation. In the next day, the 96-well microplate was rinsed in wash buffers (1×PBS; 0.05% Tween-20; pH=7.2-7.4) three times and sealed in 300 μL Reagent diluents (1×PBS; 1% Bovine serum albumin; pH=7.2-7.4) for reactions at room temperature for one hour. 100 μl standards or samples were added in the 96-well microplate which had been rinsed in wash buffers three times for reactions at room temperature in the next two hours. Having rinsed in wash buffers three times again, the 96-well microplate was sealed in 100 μL Detection antibodies for reactions at room temperature in the next two hours and further rinsed in wash buffers three times. 100 μL Streptavidin-HRP was added in the 96-well microplate for 20-minute reactions at room temperature in dark. After rinses in wash buffers three times, 100 μL substrate solutions (Tetramethylbenzidine substrates (TMB)) were added into the 96-well microplate for 20-minute reactions at room temperature in dark. With 50 μL stop solutions (2N $H_2SO_4$) added in the 96-well microplate, absorbance at the wavelength of 450 nm was measured for estimations of TNF-α, IL-6 and TGF-β1 levels according to the standard curve created with the standard solutions.

Change in the TNF-α Level

TNF-α, an inflammatory factor, is used to stimulate growth of cells effectively, activate cell differentiation and enable strong immunomodulation in an organism. The changes in rats' TNF-α level interfered by DMOC are shown in Table 4. There was no significant difference in TNF-α levels of rats between "Con" (Group 1) and "DMOC" (Group 2) ($P>0.05$). Before interference of DMOC, the TNF-α level of rats fed with HFSD and treated with STZ intraperitoneal injections was significantly higher than that of rats in "Con" and the difference has statistical significance ($P<0.01$). After interference of DMOC, the TNF-α level of rats in "DMF+DMOC" was significantly lower than that of rats in "DMF" and the difference has statistical significance ($P<0.01$). As shown by the test results, the TNF-α level which represents inflammatory cell infiltration in liver tissues due to diabetes can be moderated by interference of DMOC.

Change in the IL-6 Level

IL-6, an inflammatory factor, is used to stimulate growth of cells effectively, activate cell differentiation and enable strong immunomodulation in an organism. The changes in rats' IL-6 level interfered by DMOC are shown in Table 4. There was no significant difference in the IL-6 levels of rats between "Con" (Group 1) and "DMOC" (Group 2) ($P>0.05$). Before interference of DMOC, the IL-6 level of rats fed with HFSD and treated with STZ intraperitoneal injections was significantly higher than that of rats in "Con" and the difference has statistical significance ($P<0.01$). After interference of DMOC, the IL-6 level of rats in "DMF+DMOC" was significantly lower than that of rats in "DMF" and the difference has statistical significance ($P<0.01$). As shown by the test results, the IL-6 level which represents inflammatory cell infiltration in liver tissues due to diabetes can be moderated by interference of DMOC obviously.

Change in the TGF-β1 Level

As a dominant factor in the course of hepatic fibrosis, activated hepatic stellate cells are closely correlated with excessive depositions of extracellular matrices progressively during which TGF-β1, a pro-fibrogenic factor, over-expressing at the molecular level promotes syntheses of extracellular matrices by hepatic cells but inhibits degradations of extracellular matrices. The changes in rats' TGF-β1 level interfered by DMOC are shown in Table 4. There was no significant difference in the TGF-β1 levels of rats between "Con" and "DMOC" ($P>0.05$). Before interference of DMOC, the TGF-β1 level of rats fed with HFSD and treated with STZ intraperitoneal injections was significantly higher than that of rats in "Con" and the difference has statistical significance ($P<0.01$). After interference of DMOC, the TGF-β1 level of rats in "DMF+DMOC" was significantly lower than that of rats in "DMF" and the difference has statistical significance ($P<0.01$). As shown by the test results, the TGF-β1 level which represents more pro-fibrogenic elements in liver tissues due to diabetes can be moderated by interference of DMOC.

TABLE 4

Changes of ROS, TNF-α, IL-6 and TGF-β1 levels in rats($\bar{x} \pm s$)

| Group | N | ROS (nmol DCF/min/mg of protein) | TNF-α (ng/mL) | IL-6 (pg/mL) | TGF-β1 (pg/mL) |
|---|---|---|---|---|---|
| Con | 10 | 51.48 ± 5.52 | 6.40 ± 0.84 | 95.80 ± 12.41 | 1185.9 ± 104.8 |
| DMOC | 10 | 52.65 ± 7.14 | 6.46 ± 0.88 | 91.57 ± 8.73 | 1260.5 ± 116.0 |
| DMF | 10 | 357.75 ± 50.59## | 118.13 ± 11.11## | 1906.07 ± 211.17## | 8679.8 ± 459.0## |
| DMF + DMOC | 10 | 165.70 ± 22.97** | 54.83 ± 5.37** | 592.11 ± 5.76** | 5634.8 ± 749.1** |

Note 1:
compared with "Con" ($P < 0.01$);
Note 2:
**compared with "DMF" ($P < 0.01$)

Embodiment 3: Liver Histopathology Checked with the Hematoxylin Eosin Stain (HE Stain) Assay For checks of colors and textures of liver tissues, the 2 mm-thick liver tissues cut along the left lateral lobe, the quadrate lobe and the right lobe of a rat's liver should be fixed in 10% neutral buffered formalin, dehydrated, hyalinized, wax-impregnated and embedded for collections of 4 μm-thick sections cut from those liver tissues. The liver tissues collected from rats' same locations were placed in cryogenic vials immediately and stored in liquid nitrogen for quick freezing.

The hematoxylin eosin (HE) stain is common in staining for histopathology. Because stains with distinct structures display various binding degrees, basophilic hematoxylin and acidophilic eosin are dyed bluish violet and pink, respectively. The HE stain is used to distinguish cell nuclei from cytoplasm of a tissue in experimental steps as follows:
  (1) Fixing: The left lateral lobe, the quadrate lobe and the right lobe on a sacrificed rat's liver, each of them was 1 cm×1 cm×1 cm in size, were moistened with 0.9% normal saline and fixed with 10% neutral buffered formalin for paraffin embedding. Glass slides soaked in 1% Tween-20 solutions were cleaned in an ultrasonic oscillator for three to five 10-minute cycles, rinsed in distilled water, immersed in 95% ethyl alcohol and dried.
  (2) Sectioning: 4-6 μm thin sections cut from the liver tissues with a rotary slicer were attached to glass slides, stretched in warm water at 50-60° C. and placed in an oven at 37° C. all night for chemical staining of tissues. Paraffin-embedded tissues were kept at low temperature from 2 to 8° C. for no tissue fractured in the course of sectioning.
  (3) De-waxing: Paraffin-embedded sections were immersed in 100% xylene solutions for 15 minutes and dipped in 95% (85%, 75% and 50%) alcohol solutions in sequence for the 3-minute hydration reaction in each dipping. Then, paraffin-embedded sections were soaked in 1×PBS for three 5-minute rinse cycles.
  (4) Staining: The sections were stained with hematoxylin for three minutes and rinsed in clean water for five seconds. Then, the sections were soaked in solutions with 5 ml 12N HCl and 495 ml 95% alcohol for two seconds for de-staining during which light pink was displayed on the sections and rinsed in clean water for five more seconds. The sections were immersed in ammonia solutions (2-3 ammonia water drops added in 1000 ml water) for two seconds for neutralizing acidity of HCl solutions in previous steps and rinsed in clean water for five more seconds. Finally, the sections were stained with eosin (0.5% Eosin Y+70% alcohol) for one minute for staining of biopsies from which staining time was changed and rinsed in clean water for five more seconds.
  (5) Dehydration: The glass slides were dipped in 50% (75%, 85% and 95%) ethyl alcohol in sequence for five minutes in each dipping. Then, the glass slides were immersed in 100% xylene solutions for three minutes twice for hyalinization of tissues.
  (6) Sealing: The glass slides were covered with liposoluble mounting media as cover slips and dried for checks under an optical microscope.

The rats' liver tissues stained with the HE stain after interference of DMOC are shown in FIG. 1. There was no significant difference in rats' stained hepatic cells between "Con" and "DMOC", each of the cells featuring uniform cell sizes, structurally normal hepatic lobules and regular hepatic cords that mean no hepatic cells of an organism toxically injured by either DMOC or metabolites thereof. However, the phenomena detected at hepatic cells of rats in "DMF" were vacuolar degeneration, accumulated liver fats in tissues, thicker intercellular substances, oversized fibrous tissues, structurally injured hepatic lobules, and inflammatory cell infiltrations at portal areas around the central vein, all of which were symptoms of diabetic rats' liver injuries that can be moderated by DMOC.

Embodiment 4: Pathology of Liver Tissues Checked with the Masson's Trichrome Stain Collagenous Fibers in Liver Tissues Checked with the Masson's Trichrome Stain The Masson's trichrome stain, which was synthesized by Mr. Masson based on Mallory's triple stain and Van Gieson's stain, is effective at staining collagenous fibers selectively. The Rats' liver tissue sections fixed with 10% formalin solutions should rest all night. After the yellow color faded on the sections rinsed in water for 30 minutes, the sections were stained with Weigert's iron hematoxylin solutions for 10 minutes and rinsed in water for 15 minutes again. Then, the sections were stained with biebrich scarlet-acid fuchsin solutions for two minutes, rinsed in water slightly, re-stained with aniline blue, and soaked in phosphomolybdic-phosphotungstic acid solutions for 10-15 minutes. The sections rinsed in water slightly were re-stained with aniline blue for five minutes; the sections rinsed in water slightly again and 1% glacial acetic acid solutions for 3-5 minutes were processed in the next steps including water rinsing, dehydration, hyalinizing and sealing Finally, cell nuclei and collagenous fibers were stained black and blue, respectively.

Figure 2:
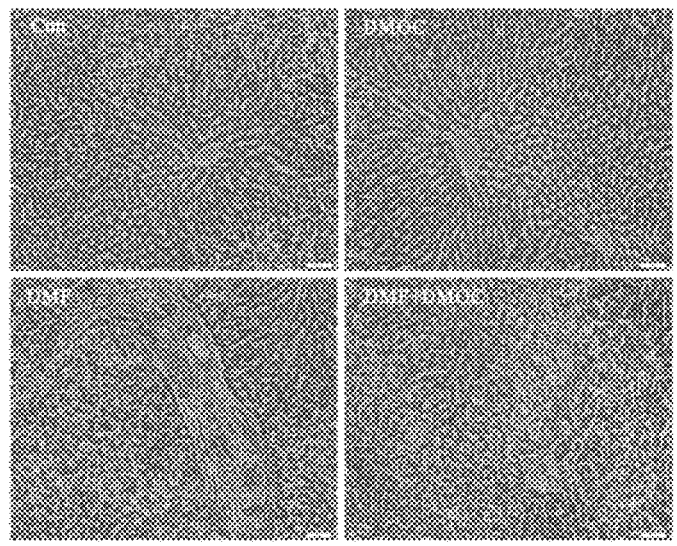
FIG. 2 Illustrates changes in rats' collagenous fibers checked with the Masson's trichrome stain assay.

After DMOC was administered to rats suffering from hepatic fibrosis by gavage for eight weeks, the rats' liver tissues stained with Masson's trichrome stain are shown in FIG. 2. First of all, the phenomena checked in liver tissues of rats in both "Con" and "DMOC" included regular hepatic lobules in structure, inerratic liver plates and fewer collagenous fibers around hepatic lobules. Secondly, collagenous fibers significantly proliferated in liver tissues and inflammatory cell infiltrations as well as jagged fibers around the portal vein were identified in rats in "DMF". Thirdly, necrosis of hepatic cells and significantly fewer inflammatory cell infiltrations and proliferations of collagenous fibers were found in rats in "DMF+DMOC". In spite of rats' liver fibrosis due to diabetes, those symptoms including necrosis of hepatic cells, inflammatory cell infiltrations, and proliferations of collagenous fibers on connective tissues can be moderated by DMOC.

Embodiment 5: Pathology of Liver Tissues Checked with the Immunohistochemistry (IHC) Assay The steps to check for α-SMA, fibrinogen, IV-Collagen, fibronectin levels in liver tissues with the IHC assay are as follows:

(1) Section drying: 4 μm-thick sections were placed in an oven at 60° C. for one hour.

(2) De-waxing & dehydration: The dried sections were de-waxed and dehydrated for staining with the Masson's trichrome stain.

(3) Removal of residual alcohol: The sections were rinsed in distilled water for three 5-minute cycles and PBS (0.01M; pH=7.4) for three 5-minute cycles.

(4) Antigen retrieval: The sections in which citric acid buffers (0.01M; pH=6.0) were added were processed at high temperature for antigen retrieval in the next five minutes, cooled down to room temperature for 30 minutes, and rinsed in PBS for three 5-minute cycles.

(5) Inactivation of endogenous peroxidase: The sections were kept in a water bath with 3% $H_2O_2$ at 37° C. for 10 minutes and rinsed in distilled water for three 5-minute cycles and PBS for three 5-minute cycles.

(6) Sealing: After liquids around liver tissues on a glass slide were wiped with a piece of thin paper, the liver tissues were circled with a rap pen and 200 μL normal goat serums were instilled in the circle. The liver tissues should be immersed totally for incubation at 37° C. in the next one hour.

(7) Incubation of antibodies: With confining liquids removed, 50 μL diluents with α-SMA, fibrinogen, IV-Collagen and fibronectin (concentration ratio=1:200) were instilled on liver tissues on each section for incubation of antibodies at 4° C. all night. In the next day, the sections kept at room temperature for 30 minutes were rinsed in PBS for three 5-minute cycles.

(8) 50 μL Reagent A, polymer enhanced reagents, were instilled on the sections for incubation at 37° C. in the next 30 minutes. With Reagent A removed, the sections were rinsed in PBS for three 5-minute cycles.

(9) 50 μL Reagent B, enzyme-labeled anti-rabbit polymers, were instilled on the sections for incubation at 37° C. in the next one hour. With Reagent B removed, the sections were rinsed in PBS for three 5-minute cycles.

(10) DAB developing: After PBS around liver tissues on a glass slide was wiped with a piece of thin paper, 50 μL 0.05% DAB solutions which were prepared immediately prior to use were instilled on the sections.

(11) The sections stained satisfactorily after checks under a microscope were rinsed in distilled water and soaked and re-stained in hematoxylin for one minute.

(12) The sections rinsed in distilled water were dehydrated conventionally as shown in steps for Masson's staining and soaked in xylene for 10 minutes. Then, the sections from which xylene around liver tissues was wiped were dried in the air and sealed with neutral balsam.

(13) The liver tissues were checked and shot with a biological microscope (Eclipse 50i, Nikon).

With collagens as the dominant ingredient, extracellular matrices which consist of protein polysaccharide, proteins in parent cells, collagen, laminin and fibronectin structurally, are synthesized increasingly but degraded modestly in the progress of hepatic fibrosis and excessively deposited in a liver which will sustain dynamic unbalance between syntheses and degradations of extracellular matrices.

Figure 3:
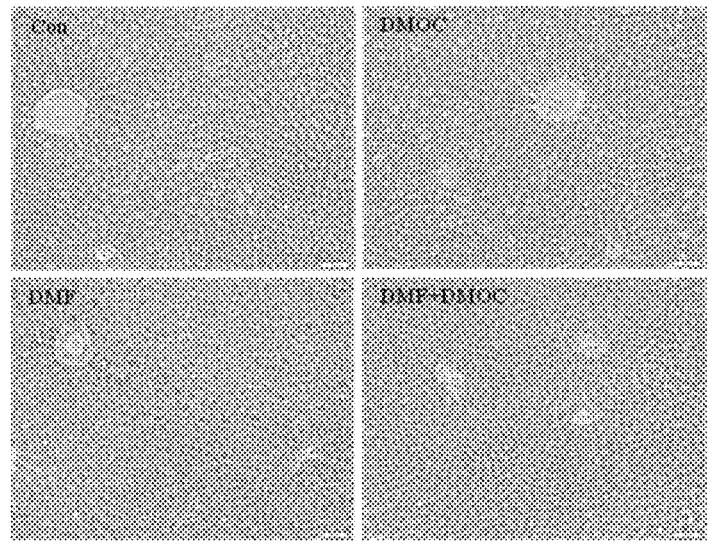
FIG. 3 Illustrates changes in rats' α-SMA level with the IHC assay.

As a vital protein in liver fibrosis, α-SMA will be over-expressing in severe fibrosis. The expressions of α-SMA checked with the IHC assay are shown in FIG. 3. α-SMA in liver tissues of rats in "Con" and "DMOC" was displayed in tan and not particularly identified at some areas; α-SMA in liver tissues of rats in "DMF" was distributed along deposited collagenous fibers mostly and over-expressing at gaps among fibers. In contrast, α-SMA in liver tissues of rats in "DMF+DMOC" expressed decreasingly and was limited to the circumference of the central vein. As shown in test results, α-SMA activated in diabetic rats with liver fibrosis can be moderated by interference of DMOC obviously.

Figure 4:
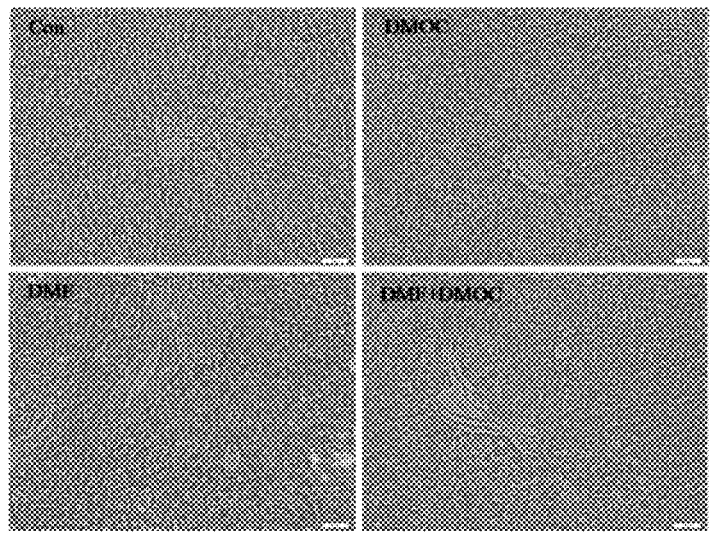
FIG. 4 Illustrates changes in rats' fibrinogen level with the IHC assay.

Distributed around the portal vein originally, fibrinogens which have been necrotic or inflammatory will diffuse to and scatter at peripheral areas gradually and widespread from fixed clusters. The expressions of fibrinogen checked with the IHC assay are shown in FIG. 4. Fibrinogens in liver tissues of rats in "Con" and "DMOC" were displayed in tan and not particularly identified at some specific areas; however, fibrinogens in liver tissues of rats in "DMF" were identified at some areas and over-expressing. In contrast, fibrinogens in liver tissues of rats in "DMF+DMOC" expressed decreasingly and were distributed limitedly. As shown in test results, fibrinogens induced by hepatocellular injuries due to diabetic rats' hepatic fibrosis can be moderated by interference of DMOC.

Figure 5:
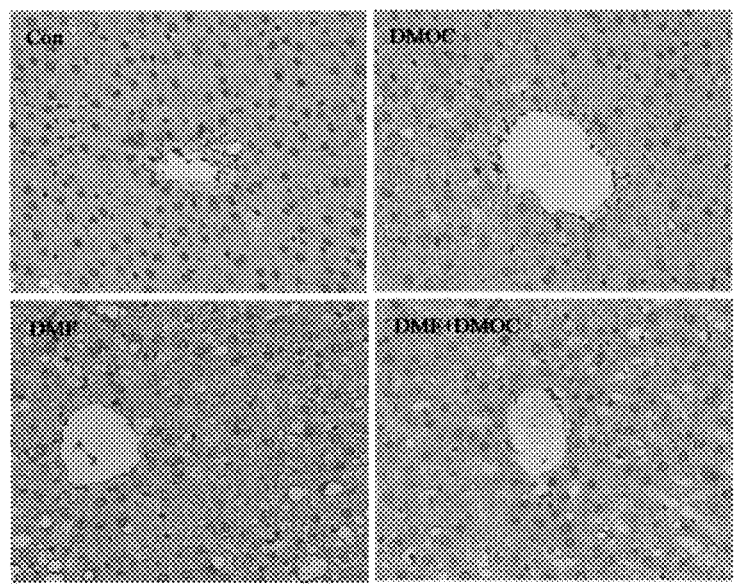
FIG. 5 Illustrates changes in rats' IV-Collagen level with the IHC assay.

As a vital protein in hepatic fibrosis, IV-Collagen will be over-expressing in severe fibrosis. The expressions of IV-Collagen checked with the IHC assay are shown in FIG. 5. IV-Collagens in liver tissues of rats in "Con" and "DMOC" were displayed in tan and not particularly identified in some specific areas; however, IV-Collagens in liver tissues of rats in "DMF" were distributed along deposited collagenous fibers mostly and over-expressing at gaps among fibers, particularly at the wider positive staining areas. In contrast, IV-Collagens in liver tissues of rats in "DMF+DMOC" expressed decreasingly and were limited to the circumference of the central vein. As shown in test results, IV-Collagens proliferated due to diabetic rats' hepatic fibrosis can be moderated by interference of DMOC obviously.

Figure 6:
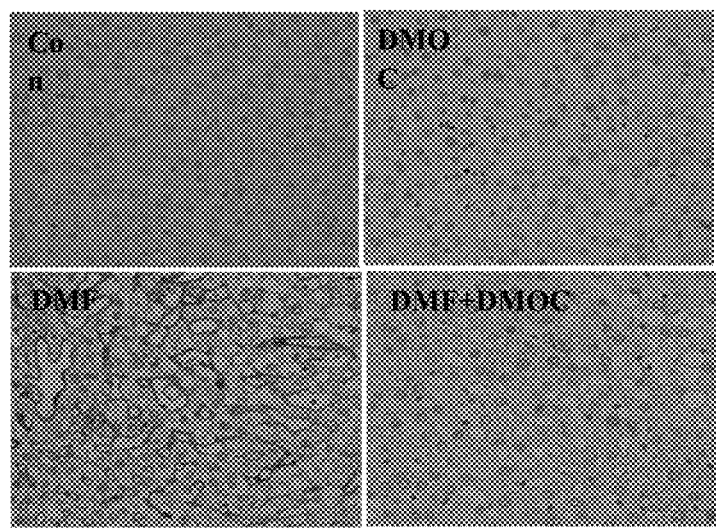
FIG. 6 Illustrates changes in rats' fibronectin level by with IHC assay.

Fibronectin, which is an extracellular glycoprotein soluble in body fluids or insoluble but remaining in extracellular matrices, is one of main cellular adhesion molecules. The expressions of fibronectins verified with the IHC assay are shown in FIG. 6. Fibronectins in liver tissues of rats in "Con" and "DMOC" were displayed in tan and not particularly identified in some specific areas; however, fibronectins in liver tissues of rats in "DMF" were overexpressing in some areas. In contrast, fibronectins in liver tissues of rats in "DMF+DMOC" expressed decreasingly and limitedly. As shown in test results, fibronectins induced by hepatocellular injuries due to diabetic rats' liver necrosis and fibrosis can be moderated by DMOC.

Embodiment 6: Protein Expressions Checked with the Western Blotting (WB) Assay

The steps of measuring Smad 2, Smad 3, pSmad 2, pSmad 3, α-SMA, MMP1, MMP 2 and MMP 9 levels with the Western blotting assay are shown as follows:

1. Preparation of protein samples of liver tissues:
   (1) Preparation of RIPA lysis buffers and protease inhibitors (phenylmethyl sulfonylfluoride (PMSF)): The RIPA lysis buffers were prepared with RIPA and PMSF (ratio=100: 1; 10 mL RIPA: one PhosSTOP tablet) immediately prior to use and placed on ice.
   (2) The liver tissues mixed with lysis buffers (1 mL lysis buffers in 100 mg liver tissues) were ground in a mortar in which liquid nitrogen was added.
   (3) The ground tissue liquids were transferred to a 1.5 mL EP tube and kept on ice for confluent lysis in the next 30 minutes.
   (4) Supernatants derived from a centrifugal machine (4° C.; 12,000 RPM; centrifuge time=15 minutes) were transferred to a new 1.5 ml EP tube in which 5×SDS-PAGE loading buffers were added based on the ratio of 4:1 for uniform mixing. The mixtures distributed in 200 µL EP tubes were boiled for denaturalization in the next 15 minutes, cooled down to room temperature, and stored in a refrigerator at −80° C. Furthermore, 5 µL total protein liquids in which no buffer liquid was added were reserved for measurement of the protein concentration.
2. Total protein level in liver tissues measured with the BCA (bicinchoninic acid) assay:
   (1) Preparation of protein markers: 6 mL protein maker agents were added into 30 mg BSA (bovine serum albumin) for complete dissolution and preparation of 5 mg/ml protein markers. 10 µL BSA-based protein markers were added into 90 µL PBS and diluted until the concentration was 0.5 mg/mL.
   (2) Preparation of BCA working reagents: According to the number of samples, Reagent A and Reagent B in a BCA protein quantification kit were completely mixed with each other (ratio=50:1). The BCA working reagents were stabilized at room temperature within 24 hours.
   (3) 0, 1, 2, 4, 8, 12, 16, 20 µL protein markers were added into wells of a 96-well microplate, each of which was filled with protein marker diluents until the volume of each well was 20 µL. The concentration levels of protein markers at wells would be 0, 0.025, 0.05, 0.1, 0.2, 0.3, 0.4 and 0.5 mg/mL.
   (4) Each sample with the appropriate volume was added into a well on a 96-well microplate in which protein marker diluents would be filled for 20 µL totally.
   (5) 200 µL BCA working reagents were added in each well and kept at 37° C. for 30 minutes. Then, the absorbance at the wavelength of 570 nm was measured.
   (6) Based on absorbance values (independent variables) and concentrations of protein markers (dependent variables) at all wells, the standard curve was developed for linear regressions and estimations of relevant coefficients. The absorbance values were substituted into the regression function for estimations of total protein levels in cell lysis buffers.
3. Separation of the target protein based on the sodium dodecyl sulfate polyacrylamide gel electrophoresis (SDS-PAGE) assay:
   (1) 10% SDS-polyacrylamide separating gels prepared were injected into a gap between two pieces of glass panes quickly with a 1 mL pipettor for no bubbles generated. Each glass pane on which 3.5 mL separating gels were added was sealed with one layer of distilled water uniformly and quickly and rested at room temperature for development of a water seal line in the next 30 minutes. With distilled water on the top removed, the residual liquids were absorbed with the edge of a piece of filter paper for the top level of separating gels unaffected.

| Ingredient | Volume of ingredients for preparation of various separating gels (mL) | | | | | |
|---|---|---|---|---|---|---|
| 10% gel | 5 | 10 | 15 | 20 | 30 | 50 |
| Distilled water | 1.3 | 2.7 | 4.0 | 5.3 | 8.0 | 13.3 |
| 30% Acr-Bis(29:1) | 1.7 | 3.3 | 5.0 | 6.7 | 10.0 | 16.7 |
| 1M Tris, pH 8.8 | 1.9 | 3.8 | 5.7 | 7.6 | 11.4 | 19.0 |
| 10% SDS | 0.05 | 0.1 | 0.15 | 0.2 | 0.3 | 0.5 |
| 10% ammonium persulfate | 0.05 | 0.1 | 0.15 | 0.2 | 0.3 | 0.5 |
| TEMED | 0.002 | 0.004 | 0.006 | 0.008 | 0.12 | 0.02 |

(2) 5% SDS-polyacrylamide stacking gels were prepared and covered on the separating gels in which a comb would be inserted for no bubble generated and solidification at room temperature.

| Ingredient | Volume of ingredients for preparation of various separating gels (mL) | | | | | |
|---|---|---|---|---|---|---|
| 5% gel | 2 | 3 | 4 | 6 | 8 | 10 |
| Distilled water | 1.4 | 2.1 | 2.7 | 4.1 | 5.5 | 6.8 |
| 30% Acr-Bis(29:1) | 0.33 | 0.5 | 0.67 | 1.0 | 1.3 | 1.7 |
| 1M Tris, pH 6.8 | 0.25 | 0.38 | 0.5 | 0.75 | 1.0 | 1.25 |
| 10% SDS | 0.02 | 0.03 | 0.04 | 0.06 | 0.08 | 0.1 |
| 10% ammonium persulfate | 0.02 | 0.03 | 0.04 | 0.06 | 0.08 | 0.1 |
| TEMED | 0.002 | 0.003 | 0.004 | 0.006 | 0.008 | 0.01 |

(3) Loading samples: With a gel slab placed in an electrophoresis chamber and electrophoresis buffers filled inside and outside the electrophoresis chamber, the gels inside the chamber were immersed in electrophoresis buffers for discharging bubbles. 20 µL samples were added into a single well on the gel slab with a pipette for SDS-PAGE in which protein markers were added simultaneously.

(4) Electrophoresis: Electrophoresis enabled at 70V for 30 minutes in the beginning was conducted at 100V continuously until the front edge of stains was close to the bottom of gels.
(5) Transfer membrane: The PVDF membrane soaked in methanol for 10 seconds was activated first and immersed in transfer buffers in which some pieces of filter paper and sponges would be placed for five minutes. With electrophoresis completed, the target band and the internal reference strips were cut on the glass gel slab removed from SDS-PAGE according to instructions for the pre-stained color protein ladder and soaked in pre-cooling transfer buffers. Referring to the length and width of the cut target band, a PVDF membrane and two pieces of thick filter papers were cut wherein the PVDF membrane was slightly greater than both the filter paper and gels and gels matched the filter paper in size. All samples were placed in an electro-transfer tank in which electrophoresis at 70V was enabled. After the samples went through stacking gels, the power for electrophoresis was increased to 80V for a period of time based on molecular weights and turned off finally.
(6) Blocking: The membrane infiltrated from top to bottom was transferred to blocking liquids, which were prepared with skim milk powders in TBST as well as 5% BSA, and shaken in a shaking table gently at 40° C. for blocking in the next two hours.
(7) Incubation of primary antibodies: The PVDF membrane accommodated in a tailored ziplock bag in which 2 mL primary antibody diluents were added was incubated in a horizontal shaking table at 4° C. all night. Note: Antibody diluents (TBST buffers) were prepared with 1% BSA, 0.5% Tween-20 and 0.01M PBS.
(8) Membrane cleaning: With the front facing upward, the PVDF membrane was cleaned in TBST in a shaking table for four 15-minute cycles.
(9) Incubation of secondary antibodies & membrane cleaning: The PVDF membrane and the corresponding secondary antibodies labeled with horseradish peroxidase (HRP), goat anti-rabbit IgG/HRP (1:2000) and goat anti-rat IgG/HRP (1:2000), were placed in a constant temperature shaking table at 37° C. for incubation in the next one hour and cleaned in TBST for four 15-minute cycles.
(10) Development based on enhanced chemiluminescence (ECL): The intensity of signals was detected with an enzymatic system based on ECL. Reagent A and Reagent B in an ECL reagent kit (ratio=1:1), 160 µL totally, were mixed for preparation of solutions immediately prior to use. Then, 160 µL solutions were instilled on the PVDF membrane uniformly. After five minutes, residual liquids were removed with a piece of filter paper. A plastic sheet at which a notch as one mark was cut on the upper-right corner was tightly attached to the transfer membrane that had been covered with a cling film and kept at room temperature in dark for 120 seconds or longer. Finally, the plastic sheet was removed, placed in developing solutions for 10 minutes and in fixing solutions for other 10 minutes, rinsed in running water for 15 minutes, and dried in the shade.
(11) Gel image analysis: The images developed with a software package for gel imaging analysis were shot by a luminescence photography system for observing and recording changes in proteins at samples and saving images. The final results were analyzed in an imaging analysis and management system, Image-ProPlus 6.0.

Statistical method: All test data in each group were presented as "mean±standard deviation ($\bar{x}$±s)" for statistic analysis according to One-way Analysis of Variance (ANOVA) and difference analysis based on Tukey Test wherein $P<0.05$ means an intergroup significant difference.

Figure 7:
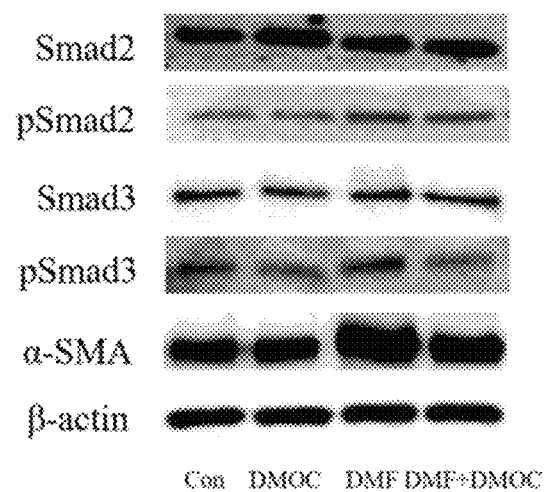
FIG. 7 Illustrates changes in rats' Smad2, pSmad2, Smad3, pSmad3 and α-SMA levels with the WB assay.

The expressions and the phosphorylation process of Smads molecules for the signaling pathway of TGF-$\beta$1→Smads inside a cell have the biological effect. Induced by signaling molecules through which the various functions of TGF-$\beta$1 are effectuated, both Type I receptors (T$\beta$R I) and Type II receptors (T$\beta$R II) on cell membranes constitute a complex for delivery of signals to direct substrates of a cell nucleus, that is, Smad 2 and Smad 3, that will be phosphorylated at T$\beta$R I for enabling liver fibrosis. Extracellular matrices secreted from α-SMA for productions of collagens as fibrous substances should be regulated by equilibrium of net reactions between α-SMA and MMPs through which fiber synthesis is greater than fibrolysis for development of so-called fibrosis tissues. Checked with the WB assay, the changes in Smad 2, pSmad 2, Smad 3, pSmad 3 and α-SMA under interference of DMOC are shown in FIG. 7. Table 5 illustrates relative densities of pSmad2/Smad2, pSmad3/Smad3 and α-SMA/β-actin. The differences of pSmad2/Smad2, pSmad3/Smad3 and α-SMA/β-actin for rats between "Con" and "DMOC" have no statistical significance ($P>0.05$). Before interference of DMOC, the relative density of pSmad2/Smad2 (pSmad3/Smad3 and α-SMA/β-actin) of rats fed with HFSD and treated with STZ intraperitoneal injections was higher than that of rats in "Con" and the difference has statistical significance ($P<0.01$). After interference of DMOC, the relative density of pSmad2/Smad2 (pSmad3/Smad3 and α-SMA/β-actin) of rats was lower than that of rats in "DMF" and the difference has statistical significance ($P<0.01$). As shown in test results, the protein expressions of pSmad2, pSmad3 and α-SMA due to diabetic rats' hepatic fibrosis can be moderated by interference of DMOC obviously in contrast to similar protein expressions of Smad 2, Smad 3 and α-SMA in all groups.

TABLE 5

Relative densities of pSmad2/Smad2, pSmad3/Smad3 and α-SMA/β-actin ($\bar{x}$ ± s)

| Group | N | Relative density of pSmad2/Smad2 | Relative density of pSmad3/Smad3 | Relative density of α-SMA/β-actin |
|---|---|---|---|---|
| Con | 10 | 0.31 ± 0.14 | 0.5677 ± 0.23 | 0.82 ± 0.09 |
| DMOC | 10 | 0.30 ± 0.15 | 0.6355 ± 0.13 | 0.85 ± 0.06 |

TABLE 5-continued

Relative densities of pSmad2/Smad2, pSmad3/Smad3 and α-SMA/β-actin ($\bar{x} \pm s$)

| Group | N | Relative density of pSmad2/Smad2 | Relative density of pSmad3/Smad3 | Relative density of α-SMA/β-actin |
|---|---|---|---|---|
| DMF | 10 | 0.71 ± 0.23## | 0.9601 ± 0.10## | 1.21 ± 0.17## |
| DMF + DMOC | 10 | 0.39 ± 0.16** | 0.6941 ± 0.16** | 0.89 ± 0.10** |

Note 1:
compared with "Con" (P < 0.01);
Note 2:
**compared with "DMF" (P < 0.01)

Changes in Protein Expressions of MMP1, MMP2 and MMP9 in Rats' Liver Tissues

Figure 8:
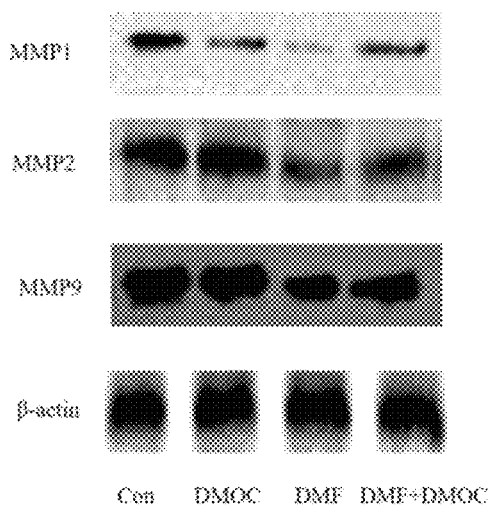
FIG. 8 Illustrates changes in rats' MMP1, MMP2 and MMP9 levels with the WB assay.

Verified with the WB assay, the changes in MMP1, MMP2 and MMP9 of rats under interference of DMOC are shown in FIG. 8. Table 6 illustrates relative densities of MMP1/β-actin, MMP2/β-actin and MMP9/β-actin. The differences of relative densities of MMP1/β-actin, MMP2/β-actin and MMP9/β-actin for rats between "Con" and "DMOC" have no statistical significance (P>0.05). Before interference of DMOC, the relative density of MMP1/β-actin (MMP2/β-actin and MMP9/β-actin) of rats fed with HFSD and treated with STZ intraperitoneal injections was lower than that of rats in "Con" and the difference has statistical significance (P<0.01). After interference of DMOC, the relative density of MMP1/β-actin (MMP2/β-actin and MMP9/β-actin) of rats in "DMF+DMOC" was significantly higher that of rats in "DMF" and the difference has statistical significance (P<0.01). As shown in test results, the protein expressions of MMP1, MMP2 and MMP9 in diabetic rats suffering from hepatic fibrosis can be promoted by DMOC which is favorable to decompositions of collagenous fibers deposited excessively.

TABLE 6

Relative densities of MMP1/β-actin, MMP2/β-actin and MMP9/β-actin ($\bar{x} \pm s$)

| Group | N | Relative density of MMP1/β-actin | Relative density of MMP2/β-actin | Relative density of MMP9/β-actin |
|---|---|---|---|---|
| Con | 10 | 0.94 ± 0.17 | 1.07 ± 0.30 | 1.25 ± .18 |
| DMOC | 10 | 0.79 ± 0.23 | 1.08 ± 0.29 | 1.09 ± 0.26 |
| DMF | 10 | 0.41 ± 0.10## | 0.60 ± 0.10## | 0.79 ± 0.06## |
| DMF + DMOC | 10 | 0.81 ± 0.10** | 0.93 ± 0.23** | 1.01 ± 0.09** |

Note 1:
compared with "Con" (P < 0.01);
Note 2:
**compared with "DMF" (P < 0.01)

Because insulin was not secreted by failed pancreatic tissues of rats which had suffered from diabetes with liver necrosis and fibrosis but were fed with HFSD and treated with STZ ("HFSD & STZ"), hyperglycemia were induced in rats on liver necrosis and fibrosis exacerbated afterwards. These results can be analogous to those symptoms such as diabetes with liver necrosis and fibrosis common in human beings who get used to Western-style diets. In the present disclosure, the herbal compound extract based on DMOC is used in order to moderate unhealthy conditions of rats suffering from diabetes with liver necrosis and fibrosis such as body weights, liver tissues' weights, weights of rats' abdominal adipose, blood glucose, blood lipid, abnormal liver functions about liver necrosis and fibrosis.

Accordingly, DMOC is effective in: moderating symptoms in liver tissues of rats suffering from diabetes with liver necrosis and fibrosis such as foamy degeneration, hepatocyte swelling, unclear boundaries among hepatic cells, narrower hepatic sinusoid, slight lymphocytes infiltration around the central vein and portal areas, and accumulations of collagenous fibers including α-SMA, fibrinogen, IV-Collagen and fibronectin; inhibiting ROS, inflammation of TNF-α/IL-6, signaling pathway of liver fibrosis from TGFβ1 to Smads to α-SMA, and protein expressions of Smad2, Smad3 and α-SMA; promoting protein expressions of MMP1, MMP2 and MMP9 and degradations of collagenous fibers.

Because any change and modification related to embodiments and/or drawings is permissible under the spirit and the scope of the present application, the claims hereinafter should cover the change and modification. Moreover, the scope of a herbal compound extract to moderate diabetes with liver necrosis and fibrosis and applications thereof in the present disclosure should not be limited in the descriptions hereinbefore.

In summary, a herbal compound extract to moderate diabetes with liver necrosis and fibrosis and applications thereof, which are innovative work in technical ideas and feature several effects in contrast to conventional substances, meet novelty and non-obviousness for patentability

What is claimed is:

1. A herbal composition for moderating diabetes with liver necrosis and fibrosis; wherein the herbal composition comprises in a therapeutically effective amount therefor a mixture of herbals obtained from an ethanolic extract of a mixture of (i) rhizome of *Dendrobium nobile* Lindl, (ii) fruiting body of *Antrodia camphorata*, (iii) root of *Panax ginseng* C. A. Mey, (iv) root of *Rehmannia glutinosa* Libosch, (v) rhizome of *Salvia miltiorrhiza* Bge., (vi) all of *Pheretima aspergillum* (E.Perrier), (vii) root of *Pueraria mirifica*, (viii) fruit of *Schisandra chinensis* (Turcz.) Baill. and (ix) rhizome of *Glycyrrhiza uralensis* Fisch.

2. The herbal composition as claimed in claim 1, wherein the herbal composition by relative unit numbers of a unit weight comprise 10 to 20 units rhizome of *Dendrobium nobile* Lindl, 6 to 12 units fruiting body of *Antrodia camphorata,* 12 to 20 units root of *Panax ginseng* C. A. Mey, 10 to 30 units root of *Rehmannia glutinosa* Libosch, 15 to 30 units rhizome of *Salvia miltiorrhiza* Bge., 6 to 12 units all of *Pheretima aspergillum*(E.Perrier), 10 to 30 units root of *Pueraria mirifica,* 8 to 15 units fruit of *Schisandra chinensis* (Turcz.) Baill and 6 to 8 units rhizome of *Glycyrrhiza uralensis* Fisch.

3. The herbal composition as claimed in claim 1, wherein the herbal composition by relative unit numbers of a unit weight comprise 20 units rhizome of *Dendrobium nobile* Lindl, 6 units fruiting body of *Antrodia camphorata,* 20 units root of *Panax ginseng* C. A. Mey, 15 units root of *Rehmannia glutinosa* Libosch, 15 units rhizome of *Salvia miltiorrhiza* Bge., 9 units all of *Pheretima aspergillum* (E.Perrier), 15 units root of *Pueraria mirifica,* 8 units fruit of *Schisandra chinensis* (Turcz.) Baill and 8 units rhizome of *Glycyrrhiza uralensis* Fisch.

4. The herbal composition as claimed in claim 1, wherein the herbal composition by relative unit numbers of a unit weight comprise 10 units rhizome of *Dendrobium nobile* Lindl, 12 units fruiting body of *Antrodia camphorata,* 20 units root of *Panax ginseng* C. A. Mey, 30 units root of *Rehmannia glutinosa* Libosch, 30 units rhizome of *Salvia miltiorrhiza* Bge., 12 units all of *Pheretima aspergillum* (E.Perrier), 10 units root of *Pueraria mirifica,* 10 units fruit of *Schisandra chinensis* (Turcz.) Baill and 8 units rhizome of *Glycyrrhiza uralensis* Fisch.

5. The herbal composition as claimed in claim 1, wherein the herbal composition by relative unit numbers of a unit weight comprise 15 units rhizome of *Dendrobium nobile* Lindl, 9 units fruiting body of *Antrodia camphorata,* 12 units root of *Panax ginseng* C. A. Mey, 10 units root of *Rehmannia glutinosa* Libosch, 15 units rhizome of *Salvia miltiorrhiza* Bge., 12 units all of *Pheretima aspergillum* (E.Perrier), 15 units root of *Pueraria mirifica,* 15 units fruit of *Schisandra chinensis* (Turcz.) Baill and 6 units rhizome of *Glycyrrhiza uralensis* Fisch.

6. The herbal composition as claimed in claim 1, wherein the herbal composition by relative unit numbers of a unit weight comprise 15 units rhizome of *Dendrobium nobile* Lindl, 9 units fruiting body of *Antrodia camphorata,* 12 units root of *Panax ginseng* C. A. Mey, 18 units root of *Rehmannia glutinosa* Libosch, 15 units rhizome of *Salvia miltiorrhiza* Bge., 6 units all of *Pheretima aspergillum* (E.Perrier), 15 units root of *Pueraria mirifica,* 15 units fruit of *Schisandra chinensis* (Turcz.) Baill and 6 units rhizome of *Glycyrrhiza uralensis* Fisch.

7. The herbal composition as claimed in claim 1, wherein the herbal composition is a powder agent for concocting each of a solution, a suspending liquid, an emulsion, syrups, a pill, a buccal tablet, a tablet, a capsule and a pastille.

8. The herbal composition as claimed in claim 1, wherein the herbal compound is a medicinal and edible formula or a food formula.

9. The herbal composition as claimed in claim 8, wherein the oral dosage by weight of the formula is 20-40 g per day.

10. The herbal composition as claimed in claim 1, wherein the herbal composition is able to moderate body weight, weight of liver tissues, weight of abdominal adipose, hyperglycemia, hyperlipidemia, liver necrosis or liver fibrosis.

11. A method of moderating diabetes with liver necrosis and fibrosis comprising administrating a herbal composition orally, wherein the herbal composition comprises in a therapeutically effective amount therefor a mixture of herbals obtained from an ethanolic extract of a mixture of (i) rhizome of *Dendrobium nobile* Lindl, (ii) fruiting body of *Antrodia camphorata*, (iii) root of *Panax ginseng* C. A. Mey, (iv) root of *Rehmannia glutinosa* Libosch, (v) rhizome of *Salvia miltiorrhiza* Bge., (vi) all of *Pheretima aspergillum* (E.Perrier), (vii) root of *Pueraria mirifica*, (viii) fruit of *Schisandra chinensis* (Turcz.) Baill. and (ix) rhizome of *Glycyrrhiza uralensis* Fisch.

12. The method as claimed in claim 11, wherein the herbal composition relative unit numbers of a unit weight comprise 10 to 20 units rhizome of Dendrobium *nobile* Lindl, 6 to 12 units fruiting body of *Antrodia camphorata,* 12 to 20 units root of *Panax ginseng* C. A. Mey, 10 to 30 units root of *Rehmannia glutinosa* Libosch, 15 to 30 units rhizome of *Salvia miltiorrhiza* Bge., 6 to 12 units all of *Pheretima aspergillum* (E.Perrier), 10 to 30 units root of *Pueraria mirifica,* 8 to 15 units fruit of *Schisandra chinensis* (Turcz.) Baill and 6 to 8 units rhizome of *Glycyrrhiza uralensis* Fisch.

13. The method as claimed claim 11, wherein the herbal composition by relative unit numbers of a unit weight comprise 20 units rhizome of *Dendrobium nobile* Lindl, 6 units fruiting body of *Antrodia camphorata,* 20 units root of *Panax ginseng* C. A. Mey, 15 units root of *Rehmannia glutinosa* Libosch, 15 units rhizome of *Salvia miltiorrhiza* Bge., 9 units all of *Pheretima aspergillum* (E.Perrier), 15 units root of *Pueraria mirifica,* 8 units fruit of *Schisandra chinensis* (Turcz.) Baill and 8 units rhizome of *Glycyrrhiza uralensis* Fisch.

14. The method as claimed in claim 11, wherein the herbal composition by relative unit numbers of a unit weight comprise 10 units rhizome of *Dendrobium nobile* Lindl, 12 units fruiting body of *Antrodia camphorata,* 20 units root of *Panax ginseng* C. A. Mey, 30 units root of *Rehmannia glutinosa* Libosch, 30 units rhizome of *Salvia miltiorrhiza* Bge., 12 units all of *Pheretima aspergillum* (E.Perrier), 10 units root of *Pueraria mirifica,* 10 units fruit of *Schisandra chinensis* (Turcz.) Baill and 8 units rhizome of *Glycyrrhiza uralensis* Fisch.

15. The method as claimed in claim 11, wherein the herbal composition by relative unit numbers of a unit weight comprise 15 units rhizome of *Dendrobium nobile* Lindl, 9 units fruiting body of *Antrodia camphorata,* 12 units root of *Panax ginseng* C. A. Mey, 10 units root of *Rehmannia glutinosa* Libosch, 15 units rhizome of *Salvia miltiorrhiza* Bge., 12 units all of *Pheretima aspergillum* (E.Perrier), 15 units root of *Pueraria mirifica,* 15 units fruit of *Schisandra chinensis* (Turcz.) Baill and 6 units rhizome of *Glycyrrhiza uralensis* Fisch.

16. The method as claimed in claim 11, wherein the herbal composition by relative unit numbers of a unit weight comprise 15 units rhizome of *Dendrobium nobile* Lindl, 9 units fruiting body of *Antrodia camphorata,* 12 units root of *Panax ginseng* C. A. Mey, 18 units root of *Rehmannia glutinosa* Libosch, 15 units rhizome of *Salvia miltiorrhiza* Bge., 6 units all of *Pheretima aspergillum* (E.Perrier), 15 units root of *Pueraria mirifica,* 15 units fruit of *Schisandra chinensis* (Turcz.) Baill and 6 units rhizome of *Glycyrrhiza uralensis* Fisch.

17. The method as claimed in claim 11, wherein moderating diabetes with liver fibrosis comprises moderating body weight, weight of liver tissues, weight of abdominal adipose, fasting blood glucose (FBG), total cholesterol (TC), triglyceride (TG), aspartate aminotransferase (AST) and alanine aminotransferase (ALT) of a patient suffering from diabetes with liver necrosis and fibrosis.

18. The method as claimed in claim 11, wherein moderating diabetes with liver necrosis and fibrosis comprises moderating at least one of foamy degeneration, hepatocyte swelling, unclear boundaries among hepatic cells, narrower hepatic sinusoid, slight lymphocytes infiltration around the central vein and portal areas, and accumulated collagenous fibers of connective tissues in liver tissues of a patient suffering from diabetes with liver fibrosis.

19. The method as claimed in claim 11, wherein moderating diabetes with liver necrosis and fibrosis comprises moderating accumulations of collagenous fibers including α-SMA, fibrinogen, IV-Collagen and fibronectin of a patient suffering from diabetes with liver fibrosis.

20. The method as claimed in claim 11, wherein moderating diabetes with liver necrosis and fibrosis comprises moderating diabetes with liver necrosis and fibrosis by inhibiting Reactive Oxygen Species (ROS), inflammation of TNF-α/IL-6, and signaling pathways of liver fibrosis from TGFβ1 to Smads to α-SMA.

21. The method as claimed in claim 11, wherein moderating diabetes with liver necrosis and fibrosis comprises promoting protein expressions of MMP1, MMP2 and MMP9, decompose more collagenous fibers and moderate diabetes with liver fibrosis by inhibiting Smad2, Smad3 and α-SMA.

\* \* \* \* \*